(12) United States Patent
Wigglesworth et al.

(10) Patent No.: US 8,097,735 B2
(45) Date of Patent: Jan. 17, 2012

(54) METHODS FOR PREPARING BENZODITHIOPHENES

(75) Inventors: Anthony James Wigglesworth, Oakville (CA); Yiliang Wu, Oakville (CA); Ping Liu, Mississauga (CA); Nan-Xing Hu, Oakville (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 13/110,973

(22) Filed: May 19, 2011

(65) Prior Publication Data

US 2011/0224402 A1     Sep. 15, 2011

Related U.S. Application Data

(62) Division of application No. 12/575,701, filed on Oct. 8, 2009, now Pat. No. 7,956,199.

(51) Int. Cl.
*C07D 409/04*     (2006.01)
(52) U.S. Cl. ........................................................ 549/43
(58) Field of Classification Search ...................... 549/43
See application file for complete search history.

(56) References Cited

U.S. PATENT DOCUMENTS

| 7,332,615 | B2 | 2/2008 | Huang et al. |
| 7,524,922 | B2 | 4/2009 | Heeney et al. |
| 2008/0102559 | A1 | 5/2008 | Ong et al. |
| 2008/0103286 | A1 | 5/2008 | Ong et al. |
| 2008/0146776 | A1 | 6/2008 | Liu et al. |

FOREIGN PATENT DOCUMENTS

| EP | 1357163 B1 | 5/2006 |
| WO | 2008011957 A1 | 1/2008 |

OTHER PUBLICATIONS

Pan et al., "Synthesis and Thin-Film Transistor Performance of Poly(4,8-didodecylbenzo[1,2-b:4,5-b']dithiophene)", Chem. Mater. 2006, 18, 3237-3241.
Beimling et al, "Synthesis of Benzo[1,2-b:4,5-b']dithiophene and its 4,8-Dimethoxy and 4,8-Dimethyl Derivatives", Chem. Ber. 119, 3198-3203 (1986).

*Primary Examiner* — Taofiq A Solola
(74) *Attorney, Agent, or Firm* — Fay Sharpe LLP

(57) ABSTRACT

Methods of adding substituents to a benzodithiophene are disclosed. A benzodithiophene is reacted with a reagent to directly add the substituent to the benzene core of the benzodithiophene. This method eliminates steps from prior process and eliminates the need for hydrogenation, allowing for a safer and more scaleable process. The resulting benzodithiophenes are suitable for use in semiconductor polymers and have no loss of performance.

18 Claims, 1 Drawing Sheet

METHODS FOR PREPARING BENZODITHIOPHENES

CROSS-REFERENCE TO RELATED APPLICATIONS

This application is a divisional of U.S. patent application Ser. No. 12/575,701, filed Oct. 8, 2009, now U.S. Pat. No. 7,956,199. The disclosure of this application is hereby fully incorporated by reference herein.

BACKGROUND

The present disclosure relates, in various embodiments, to polymers and methods for preparing such polymers. The polymers may be semiconductor polymers and organic semiconductors suitable for use in electronic devices, such as thin film transistors ("TFT"s) and organic solar cells. Also included are devices comprising these polymers.

Thin film transistors (TFTs) are fundamental components in modern-age electronics, including, for example, sensors, image scanners, and electronic display devices. It is generally desired to make TFTs which have not only much lower manufacturing costs, but also appealing mechanical properties such as being physically compact, lightweight, and flexible.

TFTs are generally composed of a supporting substrate, three electrically conductive electrodes (gate, source and drain electrodes), a channel semiconductor layer, and an electrically insulating gate dielectric layer separating the gate electrode from the semiconductor layer.

It is desirable to improve the performance of known TFTs. Performance can be measured by at least two properties: the mobility and the on/off ratio. The mobility is measured in units of $cm^2/V \cdot sec$; higher mobility is desired. The on/off ratio is the ratio between the amount of current that leaks through the TFT in the off state versus the current that runs through the TFT in the on state. Typically, a higher on/off ratio is more desirable.

One approach to producing flexible TFTs is the use of organic polymers to make organic TFTs (OTFTs). There is high demand for solution processable, air stable p-type semiconductor polymer compositions for use in the printed electronics industry. However, it would be desirable for methods and processes that produce such semiconductor polymer compositions to be more efficient, safer, and/or scalable.

BRIEF DESCRIPTION

Disclosed in various embodiments herein are methods for making semiconductor polymer compositions. In particular, the methods are useful for producing benzo[1,2-b:4,5-b']dithiophenes, also known as benzodithiophenes or BDTs. These methods allow for the preparation of electronics grade materials without compromising the performance of the resulting polymer.

Disclosed in embodiments are methods of producing a 4,8-disubstituted benzodithiophene of Formula (I):

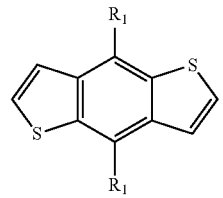

Formula (I)

wherein $R_1$ is independently selected from alkyl, aryl, and heteroaryl; the method comprising: reacting a benzoquinone-dithiophene with a reagent having a pKa of at least 35 and having the formula M-$R_1$, wherein M is MgX or Li, X is a halogen, and $R_1$ is alkyl, aryl, or heteroaryl; and reducing the resulting intermediate to form the 4,8-disubstituted benzodithiophene of Formula (I). $R_1$ may be linear alkyl or branched alkyl. $R_1$ may also have from 1 to about 24 carbon atoms.

The reduction of the intermediate may be performed using a metal chloride in an acidic solution, the metal chloride being selected from the group consisting of tin chloride, zinc chloride, or iron chloride.

The reagent may be dissolved in a solvent selected from hydrocarbon solvents, aromatic solvents, diethyl ether, tert-butylmethyl ether, tetrahydrofuran, 1,4-dioxane, and mixtures thereof to form a reagent solution. A salt or organic additive, such as LiCl or LiBr, may also be added to the reagent solution to modify the reactivity of the reagent.

The reaction is performed by adding the benzoquinone-dithiophene to the reagent solution. The combined benzoquinone-dithiophene and reagent can be heated to a temperature of from about 20° C. to about 140° C. The heating may occur for a period of at least 30 minutes. The molar ratio of the reagent to the benzoquinone-dithiophene may be from about 2:1 to about 4:1.

The reduction may comprise heating to a temperature of from about 20° C. to about 140° C. This heating may also occur for a period of at least 30 minutes.

The method may further comprise purifying the 4,8-disubstituted benzodithiophene using column chromatography through silica gel and recrystallization, and combinations thereof.

Disclosed in embodiments are methods of producing a semiconductor polymer of Formula (II):

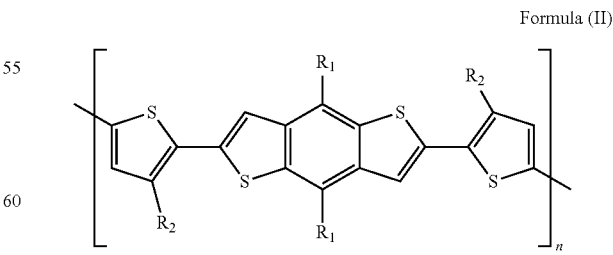

Formula (II)

wherein each $R_1$ and each $R_2$ is independently selected from alkyl, aryl, and heteroaryl; and n is from 2 to about 5,000; the method comprising: reacting a benzoquinone-dithiophene with a reagent of the formula M-$R_1$, wherein M is MgX or Li, X is a halogen, and $R_1$ is alkyl, aryl, or heteroaryl; reducing the resulting intermediate to form the 4,8-disubstituted benzodithiophene of Formula (I):

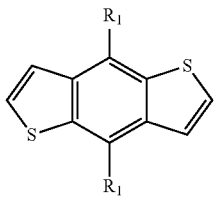

Formula (I)

coupling a 3-$R_2$-thiophene to the 2 and 6 positions of the benzodithiophene, wherein $R_2$ is alkyl, aryl, or heteroaryl, to obtain a repeating unit; and polymerizing the repeating unit to obtain the polymer of Formula (II).

$R_1$ and $R_2$ may have from about 1 to about 24 carbon atoms. Desirably, no hydrogen gas ($H_2$) is used in the method.

The reduction of the intermediate is performed using tin chloride in an acidic solution in specific embodiments.

The 4,8-disubstituted benzodithiophene of Formula (I) can be coupled to 3-$R_2$-thiophene at the 2 and 6 positions using a palladium, nickel, or iron catalyzed cross-coupling reaction.

The reacting can be performed by adding the benzoquinone-dithiophene to the reagent solution. The benzoquinone-dithiophene is combined with the reagent solution and heated to a temperature of from about 20° C. to about 140° C., including a range of from about 40° C. to about 80° C. The heating may occur for a period of from at least 30 minutes to about 4 hours. The reacting may occur in an inert atmosphere.

The molar ratio of the reagent to the benzoquinonedithiophene may be from about 2:1 to about 4:1.

The reducing may comprise heating to a temperature of from about 20° C. to about 140° C., including from about 40° C. to about 80° C., for a period of from at least 30 minutes to about 24 hours.

The method may further comprise purifying the 4,8-disubstituted benzodithiophene. Sometimes, a yield of at least about 30% is obtained. The repeating unit of formula (II), when n=1, can also be purified to a minimum HPLC purity of 94% using a combination of column chromatography through silica gel, alumina, or combinations thereof, and recrystallization.

Disclosed in other embodiments is a semiconductor polymer of Formula (II):

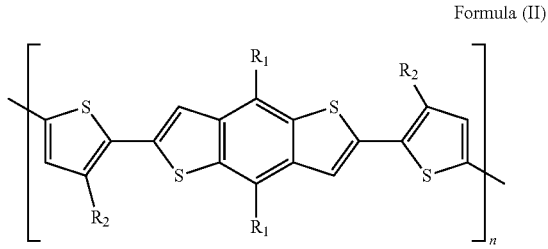

Formula (II)

wherein each $R_1$ and each $R_2$ is independently selected from alkyl, aryl, and heteroaryl; and n is from 2 to about 5,000; wherein the polymer is produced by: reacting a benzoquinone-dithiophene with a reagent of the formula M-$R_1$, wherein M is MgX or Li, X is a halogen, and $R_1$ is alkyl, aryl, or heteroaryl; reducing the resulting intermediate to form the 4,8-disubstituted benzodithiophene of Formula (I):

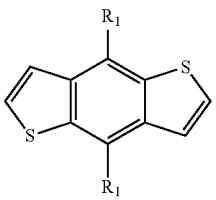

Formula (I)

coupling a 3-$R_2$-thiophene to the 2 and 6 positions of the benzodithiophene, wherein $R_2$ is alkyl, aryl, or heteroaryl, to obtain a repeating unit; and polymerizing the repeating unit to obtain the polymer of Formula (II).

Also disclosed is an electronic device, such as a thin film transistor, comprising a semiconductor layer, the semiconductor layer containing the semiconductor polymer of Formula (II).

Also disclosed is a method for obtaining a 4,8-disubstitutedbenzo[1,2-b:4,5-b']dithiophene, comprising, in sequence: preparing a mixture comprising a reagent of the formula M-$R_1$, wherein M is MgX or Li, X is a halogen, and $R_1$ is alkyl, aryl, or heteroaryl; adding a benzo[1,2-b:4,5-b']dithiophene-4,8-dione to the mixture; heating the mixture; quenching the mixture and cooling the mixture; adding a solution of tin chloride and acid to the mixture; heating the mixture; quenching the mixture and cooling the mixture to obtain an organic layer and an aqueous layer; and purifying the organic layer to obtain the 4,8-disubstitutedbenzo[1,2-b:4,5-b']dithiophene.

These and other non-limiting aspects of the present disclosure are more particularly described below.

BRIEF DESCRIPTION OF THE DRAWINGS

The following is a brief description of the drawings, which are presented for the purpose of illustrating the exemplary embodiments disclosed herein and not for the purpose of limiting the same.

DETAILED DESCRIPTION

Figure 2:
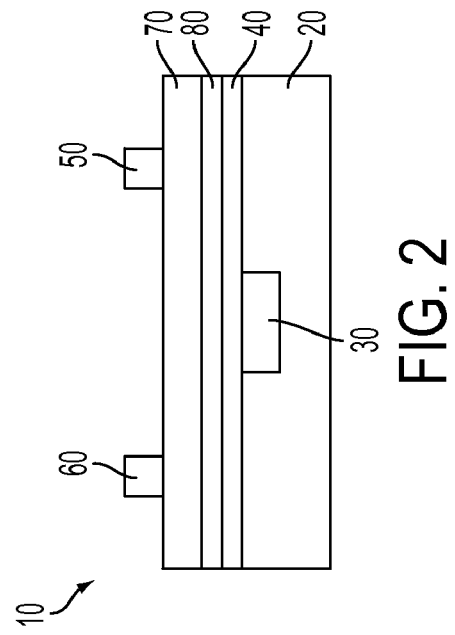
FIG. 2 is a second exemplary embodiment of an OTFT of the present disclosure.

A more complete understanding of the components, processes, and apparatuses disclosed herein can be obtained by reference to the accompanying figures. These figures are merely schematic representations based on convenience and the ease of demonstrating the present development and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range "from about 2 to about 4" also discloses the range "from 2 to 4."

The present disclosure relates to processes for preparing benzodithiophene semiconductor polymers. They are suitable for use as a semiconductor layer in, for example, organic thin film transistors (OTFTs).

Figure 1:
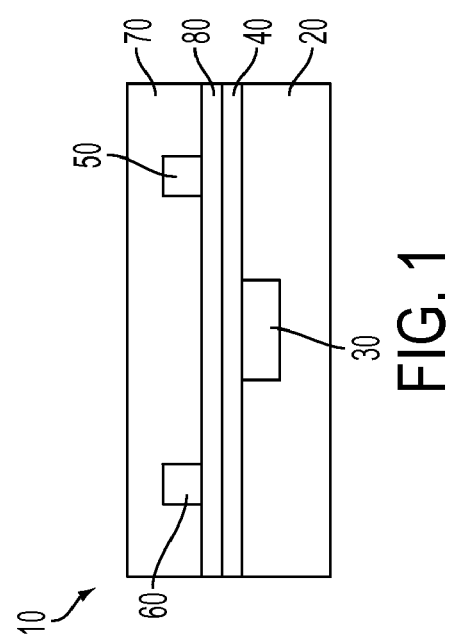
FIG. 1 is a first exemplary embodiment of an OTFT of the present disclosure.

FIG. 1 illustrates a first OTFT embodiment or configuration. The OTFT 10 comprises a substrate 20 in contact with the gate electrode 30 and a dielectric layer 40. Although here the gate electrode 30 is depicted within the substrate 20, this is not required. However, of some importance is that the dielectric layer 40 separates the gate electrode 30 from the source electrode 50, drain electrode 60, and the semiconductor layer 70. The source electrode 50 contacts the semiconductor layer 70. The drain electrode 60 also contacts the semiconductor layer 70. The semiconductor layer 70 runs over and between the source and drain electrodes 50 and 60. Interfacial layer 80 is located between dielectric layer 40 and semiconductor layer 70.

FIG. 2 illustrates a second OTFT embodiment or configuration. The OTFT 10 comprises a substrate 20 in contact with the gate electrode 30 and a dielectric layer 40. The semiconductor layer 70 is placed over or on top of the dielectric layer 40 and separates it from the source and drain electrodes 50 and 60. Interfacial layer 80 is located between dielectric layer 40 and semiconductor layer 70.

Figure 3:
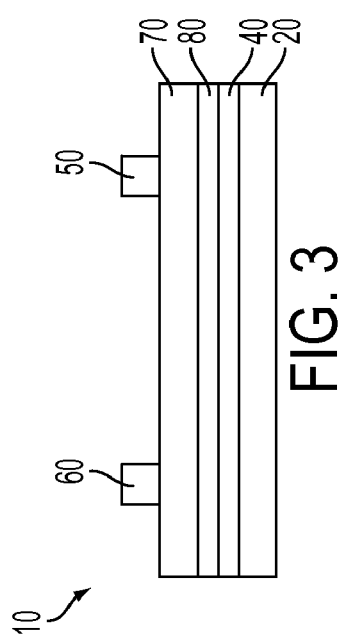
FIG. 3 is a third exemplary embodiment of an OTFT of the present disclosure.

FIG. 3 illustrates a third OTFT embodiment or configuration. The OTFT 10 comprises a substrate 20 which also acts as the gate electrode and is in contact with a dielectric layer 40. The semiconductor layer 70 is placed over or on top of the dielectric layer 40 and separates it from the source and drain electrodes 50 and 60. Interfacial layer 80 is located between dielectric layer 40 and semiconductor layer 70.

Figure 4:
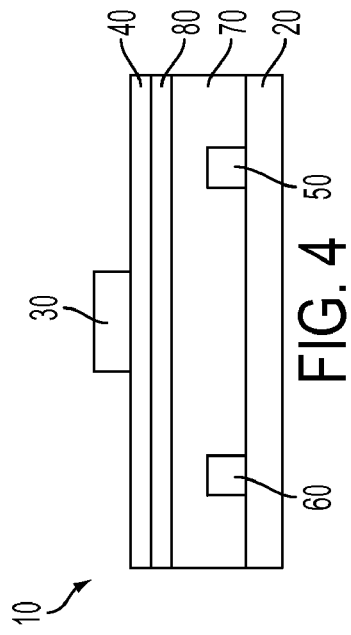
FIG. 4 is a fourth exemplary embodiment of an OTFT of the present disclosure.

FIG. 4 illustrates a fourth OTFT embodiment or configuration. The OTFT 10 comprises a substrate 20 in contact with the source electrode 50, drain electrode 60, and the semiconductor layer 70. The semiconductor layer 70 runs over and between the source and drain electrodes 50 and 60. The dielectric layer 40 is on top of the semiconductor layer 70. The gate electrode 30 is on top of the dielectric layer 40 and does not contact the semiconductor layer 70. Interfacial layer 80 is located between dielectric layer 40 and semiconductor layer 70.

Benzodithiophene based semiconductor polymers are important materials for organic thin-film transistors and organic solar cells. This important material is soluble (allowing for ease of use in manufacturing) and exhibits high field-effect mobility in OTFTs without requiring a thermal annealing step during device fabrication. Benzodithiophenes (BDTs) are generally referred to using the following structure:

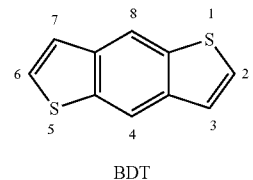

BDT

The benzodithiophene moiety core itself has very low solubility in organic solvents. However, with some modification, soluble BDT-containing polymers can be obtained, such as the polymer of Formula (II):

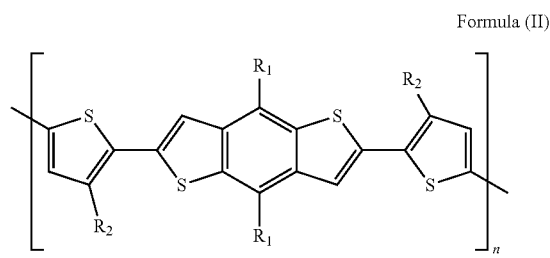

Formula (II)

wherein each $R_1$ and each $R_2$ is independently selected from alkyl, aryl, and heteroaryl; and n is the number of repeating units and is from 2 to about 5,000.

The term "alkyl" refers to a substituent composed entirely of carbon atoms and hydrogen atoms which is fully saturated and of the formula $C_nH_{2n+1}$. An alkyl chain may be linear or branched. The term "aryl" refers to a substituent composed entirely of carbon atoms and hydrogen atoms which is aromatic. The term "heteroaryl" refers to a substituent composed of carbon atoms, hydrogen atoms, and one or more heteroatoms (O, N, S) which is aromatic.

The polymer of Formula (II) may also be known in specific embodiments as poly(4,8-dialkyl-2,6-bis(3-alkylthiophen-2-yl)benzo[1,2-b:4,5-b']dithiophene). In further specific embodiments, $R_1$ and $R_2$ are each alkyl having from 1 to about 24 carbon atoms. In other embodiments, $R_1$ and $R_2$ are identical to each other. In one specific example, $R_1$ and $R_2$ are each —$C_{12}H_{25}$.

One known process for preparing an alkylated benzodithiophene core is shown in Scheme 1, illustrated using the addition of a —$C_{12}H_{25}$ chain. Beginning with a benzoquinone starting material, alkyl sidechains are added to the 4 and 8 positions using an alkynylmagnesium or alkynyllithium reagent (in Scheme 1, M is MgX or Li, where X is a halogen) and reduction of the diols by use of tin(II) chloride ($SnCl_2$). The alkynyl linkage is subsequently reduced with $H_2$ gas. This three-step process uses flammable hydrogen gas, which is generally considered unsafe. In addition, this process is difficult to scale above lab-bench amounts (i.e. grams).

Scheme 1

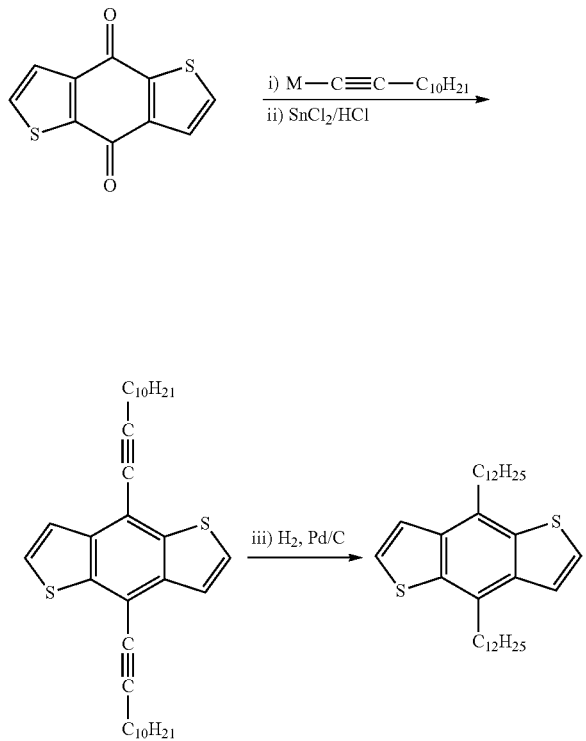

In this disclosure, the process of alkylating the benzodithiophene core is shown in Scheme 2, again illustrated using the addition of a —$C_{12}H_{25}$ chain. Beginning with a p-benzoquinone starting material (i.e. a benzodithiophene-4,8-dione), the —$C_{12}H_{25}$ chain is directly added onto the central benzene ring at the 4 and 8 positions using an organomagnesium or organolithium reagent, (in Scheme 2, M is MgX or Li, where X is a halogen), the organic portion of the reagent being alkyl, aryl, or heteroaryl. This is followed by a reductive aromatization step. This two-step process simplifies purification and eliminates reactions using hydrogen gas. Another advantage is that this process allows the addition of substituents, such as branched alkyl chains or aryl rings, which are otherwise unaccessable (i.e. cannot be placed on the 4 and 8 locations) using the prior art shown in Scheme 1.

Scheme 2

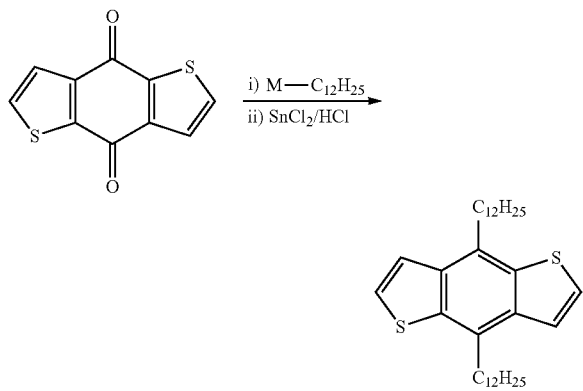

The processes of the present disclosure are illustrated more broadly in Scheme 3:

Scheme 3

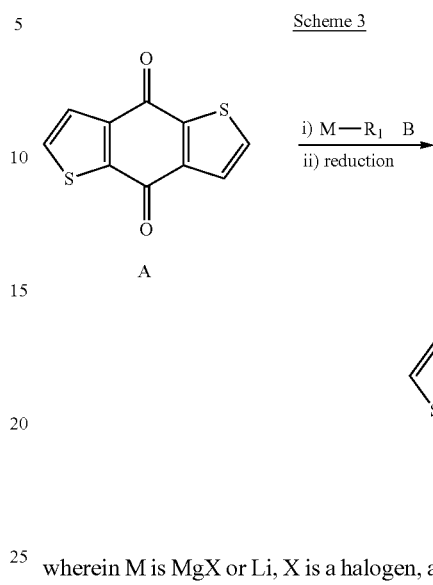

wherein M is MgX or Li, X is a halogen, and $R_1$ is alkyl, aryl, or heteroaryl. The starting benzoquinone-dithiophene or benzodithiophene-4,8-dione A is reacted with reagent B to obtain $R_1$ substituents at the 4 and 8 positions to obtain an intermediate compound (not shown). The intermediate compound is then reduced to form the 4,8-disubstituted benzodithiophene C.

The organomagnesium or organolithium reagent M-$R_1$ has a pKa of at least 35, i.e. the pKa is 35 or higher. In other words, the reagent is very alkaline. An exemplary reagent is dodecylmagnesium bromide, which has a pKa of about 50. The pKa of benzoquinone-dithiophene is about 35. This large pKa difference generally leads to undesired side acid-base reactions which reduce the yield of the desired BDT. However, careful selection of the reaction process produces BDTs in reasonable yields. The prior art process shown in Scheme 1 utilizes an alkynylmagnesium or alkynyllithium reagent with a pKa of about 25 which avoids these competing side reactions.

In the reduction step, generally any reducing agent which does not affect the identity of $R_1$ can be used. In embodiments, the reduction is performed using a metal chloride in an acidic solution (typically via addition of HCl). Exemplary metal chlorides include tin chloride, zinc chloride, and iron chloride. However, in particular embodiments, $SnCl_2$ in an acidic solution is used.

The reagent is typically dissolved in a solvent to form a reagent solution. The solvent may be a hydrocarbon solvent, an aromatic solvent, diethyl ether, tert-butylmethyl ether, tetrahydrofuran (THF), 1,4-dioxane, or a mixture thereof. Exemplary solvents include cyclohexane, xylene, hexane, heptane, and toluene. In particular embodiments, the solvent is an anhydrous ethereal solvent.

In general the benzoquinone-dithiophene is added to a solution of the organomagnesium or organolithium reagent. The concentration of the organomagnesium or organolithium reagent may be from about 0.1 M to about 1.0 M. The reaction is typically heated to a range of from about 20° C. to about 140° C., including from about 40° C. to about 80° C. The heating typically lasts for a period of at least 30 minutes to about 4 hours. In other embodiments, the heating last for at least 1 hour. The reaction is cooled to room temperature and the excess organomagnesium or organolithium reagent is quenched with water. The reaction is then treated with an acidic solution of a metal chloride. The concentration of the metal chloride is from about 1 M to about 3 M dissolved in a 10 vol % hydrochloric acid solution. The reaction is typically heated a range of from about 20° C. to about 140° C., including from about 40° C. to about 80° C. The reaction can be heated for a period of at least 30 minutes, including from about 2 hours to about 24 hours. The reaction is cooled to room temperature and the product C is isolated and purified using standard methods known in the art. For example, the product can be purified by a combination of column chromatography and recrystallization. The column may use, for example, silica gel or alumina. In some embodiments, column chromatography and recrystallization are used to achieve a minimum HPLC purity of 94%.

This process has been optimized and repeated several times and gives a stable yield of around 30%.

In particular embodiments, the organomagnesium/organolithium reagent B is dissolved in a solvent like hexane or an ethereal solvent/ether containing solvent, such as diethyl ether, tetrahydrofuran (THF), 1,4-dioxane, or tert-butylmethyl ether (TBME). The starting benzoquinone-dithiophene A is then added to the solution to begin the reaction. In particular embodiments, the reaction of the benzoquinone-dithiophene and the reagent occurs in an inert atmosphere, for example argon or nitrogen. The molar ratio of the reagent to the benzoquinone-dithiophene (reagent:benzoquinone-dithiophene) may be from about 2:1 to about 4:1, to ensure complete addition of substituents to the 4 and 8 positions.

The order of addition of the various ingredients is not important. For example, the organomagnesium/organolithium reagent can be added to a suspension of the benzoquinone-dithiophene in an ethereal solvent and the reaction can be completed as described previously with yields of around 30%.

Salts or other organic additives which modify the reactivity of organomagnesium reagents, such as LiCl or LiBr, do not affect the yield of the process and can be added to the reagent solution as well. This process has been demonstrated on a 5 gram scale with similar yields and it is expected that larger batch sizes will give consistent and reproducible yields in the 30% range.

The alkylated benzodithiophene core can then be used to form semiconductor polymers using methods known in the art. Those semiconductor polymers can be used to form semiconductor layers in, for example, organic thin film transistors.

For example, the polymer of Formula (II) can be formed as shown below in Scheme 4:

Scheme 4

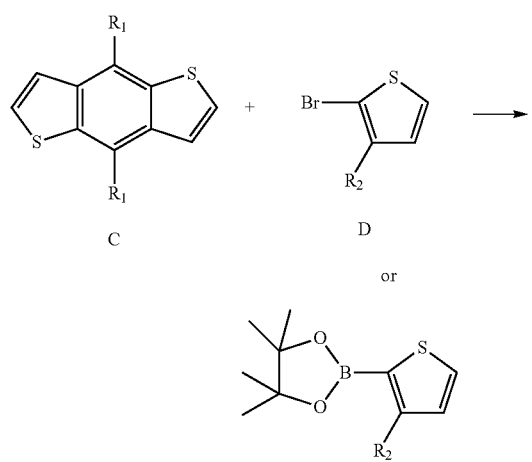

C

D or

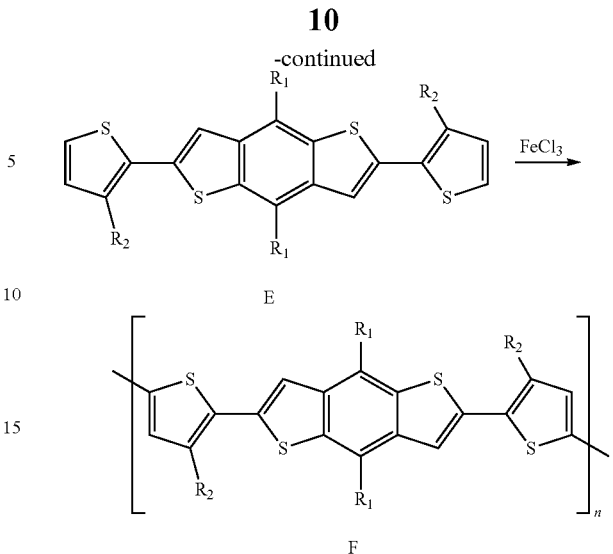

E

F

Briefly, a 3-$R_2$-thiophene D is coupled to the 2 and 6 positions of the 4,8-disubstituted benzodithiophene C to obtain the repeating unit E. For example, a palladium catalyzed cross-coupling reaction can be used to couple C and D together. The repeating unit is then purified, for example through column chromatography and recrystallization, to achieve a minimum HPLC purity of 94%. The repeating unit is then polymerized to obtain polymer F. The polymerization may be, for example, an oxidative coupling reaction mediated by $FeCl_3$.

If desired, the semiconductor layer may further comprise another organic semiconductor material. Examples of other organic semiconductor materials include but are not limited to acenes, such as anthracene, tetracene, pentacene, and their substituted derivatives, perylenes, fullerenes, oligothiophenes, other semiconductor polymers such as triarylamine polymers, polyindolocarbazole, polycarbazole, polyacenes, polyfluorene, polythiophenes and their substituted derivatives, phthalocyanines such as copper phthalocyanines or zinc phthalocyanines and their substituted derivatives.

The semiconductor layer is from about 5 nm to about 1000 nm thick, especially from about 10 nm to about 100 nm thick. The semiconductor layer can be formed by any suitable method. However, the semiconductor layer is generally formed from a liquid composition, such as a dispersion or solution, and then deposited onto the substrate of the transistor. Exemplary deposition methods include liquid deposition such as spin coating, dip coating, blade coating, rod coating, screen printing, stamping, ink jet printing, and the like, and other conventional processes known in the art.

The substrate may be composed of materials including but not limited to silicon, glass plate, plastic film or sheet. For structurally flexible devices, plastic substrate, such as for example polyester, polycarbonate, polyimide sheets and the like may be used. The thickness of the substrate may be from about 10 micrometers to over 10 millimeters with an exemplary thickness being from about 50 micrometers to about 5 millimeters, especially for a flexible plastic substrate and from about 0.5 to about 10 millimeters for a rigid substrate such as glass or silicon.

The gate electrode is composed of an electrically conductive material. It can be a thin metal film, a conducting polymer film, a conducting film made from conducting ink or paste or the substrate itself, for example heavily doped silicon. Examples of gate electrode materials include but are not restricted to aluminum, gold, silver, chromium, indium tin oxide, conductive polymers such as polystyrene sulfonate-doped poly(3,4-ethylenedioxythiophene) (PSS-PEDOT), and conducting ink/paste comprised of carbon black/graphite or silver colloids. The gate electrode can be prepared by vacuum evaporation, sputtering of metals or conductive metal oxides, conventional lithography and etching, chemical vapor deposition, spin coating, casting or printing, or other deposition processes. The thickness of the gate electrode ranges from about 10 to about 500 nanometers for metal films and from about 0.5 to about 10 micrometers for conductive polymers.

The dielectric layer generally can be an inorganic material film, an organic polymer film, or an organic-inorganic composite film. Examples of inorganic materials suitable as the dielectric layer include silicon oxide, silicon nitride, aluminum oxide, barium titanate, barium zirconium titanate and the like. Examples of suitable organic polymers include polyesters, polycarbonates, poly(vinyl phenol), polyimides, polystyrene, polymethacrylates, polyacrylates, epoxy resin and the like. The thickness of the dielectric layer depends on the dielectric constant of the material used and can be, for example, from about 10 nanometers to about 500 nanometers. The dielectric layer may have a conductivity that is, for example, less than about $10^{-12}$ Siemens per centimeter (S/cm). The dielectric layer is formed using conventional processes known in the art, including those processes described in forming the gate electrode.

If desired, an interfacial layer may be placed between the dielectric layer and the semiconductor layer. As charge transport in an organic thin film transistor occurs at the interface of these two layers, the interfacial layer may influence the TFT's properties. Exemplary interfacial layers may be formed from silanes, such as those described in U.S. patent application Ser. No. 12/101,942, filed Apr. 11, 2008.

Typical materials suitable for use as source and drain electrodes include those of the gate electrode materials such as gold, silver, nickel, aluminum, platinum, conducting polymers, and conducting inks. In specific embodiments, the electrode materials provide low contact resistance to the semiconductor. Typical thicknesses are about, for example, from about 40 nanometers to about 1 micrometer with a more specific thickness being about 100 to about 400 nanometers. The OTFT devices of the present disclosure contain a semiconductor channel. The semiconductor channel width may be, for example, from about 5 micrometers to about 5 millimeters with a specific channel width being about 100 micrometers to about 1 millimeter. The semiconductor channel length may be, for example, from about 1 micrometer to about 1 millimeter with a more specific channel length being from about 5 micrometers to about 100 micrometers.

The source electrode is grounded and a bias voltage of, for example, about 0 volt to about 80 volts is applied to the drain electrode to collect the charge carriers transported across the semiconductor channel when a voltage of, for example, about +10 volts to about −80 volts is applied to the gate electrode. The electrodes may be formed or deposited using conventional processes known in the art.

If desired, a barrier layer may also be deposited on top of the TFT to protect it from environmental conditions, such as light, oxygen and moisture, etc. which can degrade its electrical properties. Such barrier layers are known in the art and may simply consist of polymers.

The various components of the OTFT may be deposited upon the substrate in any order, as is seen in the Figures. The term "upon the substrate" should not be construed as requiring that each component directly contact the substrate. The term should be construed as describing the location of a component relative to the substrate. Generally, however, the gate electrode and the semiconductor layer should both be in contact with the dielectric layer. In addition, the source and drain electrodes should both be in contact with the semiconductor layer. The semiconductor polymer formed by the methods of the present disclosure may be deposited onto any appropriate component of an organic thin-film transistor to form a semiconductor layer of that transistor.

The resulting transistor may have, in embodiments, a mobility of 0.2 $cm^2/V \cdot sec$ or greater.

The following examples illustrate the methods of the present disclosure. The examples are merely illustrative and are not intended to limit the present disclosure with regard to the materials, conditions, or process parameters set forth therein. All parts are percentages by weight unless otherwise indicated.

EXAMPLES

Example 1

In a 500 mL round-bottomed flask, anhydrous tetrahydrofuran (150 mL) was treated with a 1M solution of dodecyl magnesium bromide (34 mL, 34 mmol). Solid 4,8-dehydrobenzo[1,2-b:4,5-b']dithiophene-4,8-dione (2.50 grams, 11.4 mmol) was added in one portion and the reaction was heated to 60° C. under an argon atmosphere. After 90 minutes, the heating bath was removed and the reaction was cooled to room temperature and carefully quenched with water (20 mL). The reaction was treated with a solution of tin(II) chloride (12.91 grams, 68.1 mmol) in 10 vol % hydrochloric acid solution (30 mL) and was heated to 60° C. After 18 hours, the heating bath was removed and the reaction was cooled to room temperature. The layers were separated and the organic layer was dried (using $MgSO_4$), filtered and concentrated using a rotary evaporator. The crude product was passed through a short $SiO_2$ plug using hexanes as eluent, and the product was recrystallized from hexanes yielding 4,8-didodecylbenzo[1,2-b:4,5-b']dithiophene as a white solid (1.7 grams, 28% yield). The structure was confirmed by $^1H$ and $^{13}C$ NMR spectroscopy.

Example 2

In a 500 mL round-bottomed flask 4,8-dehydrobenzo[1,2-b:4,5-b']dithiophene-4,8-dione (2.50 grams, 11.4 mmol) was suspended in anhydrous tert-butylmethyl ether (150 mL). The suspension was treated dropwise with a 1M solution of dodecylmagnesium bromide (45.4 mL, 45.4 mmol) under an argon atmosphere. After 90 minutes, the heating bath was removed and the reaction was cooled to room temperature and carefully quenched with water (20 mL). The reaction was treated with a solution of tin(II) chloride (12.9 grams, 68.1 mmol) in 10 vol % hydrochloric acid solution (30 mL) and heated to 50° C. After 4 hours, the heating source was removed and the reaction was cooled to room temperature. The layers were separated and the organic layer was dried (using $MgSO_4$), filtered and concentrated using a rotary evaporator. The crude product was passed through a short $SiO_2$ plug using hexanes as eluent, and the product was recrystallized from hexanes yielding 4,8-didodecylbenzo[1,2-b:4,5-b']dithiophene as a white solid (1.7 grams, 28% yield). The structure was confirmed by $^1H$ and $^{13}C$ NMR spectroscopy.

Example 3

In a 500 mL 3-necked round-bottomed flask lithium chloride (1.45 grams, 34.0 mmol) was dissolved in anhydrous THF (150 ml) and treated with a 1M solution of dodecylmagnesium bromide (34.0 ml, 34.0 mmol) under an argon atmosphere. The reaction was treated with solid 4,8-dehydrobenzo[1,2-b:4,5-b']dithiophene-4,8-dione (2.5 grams, 11.4 mmol) and stirred at room temperature. After 30 minutes, the reaction was heated to 65° C. After 1 hour, the heating bath was removed and the reaction was cooled to room temperature and carefully quenched with water (20 mL). The reaction was treated with a solution of tin(II) chloride (10.76 g, 56.7 mmol) in 10 vol % HCl (30.0 ml) was added in one portion and the reaction was heated to 65° C. After 3 hours, the heating bath was removed and the reaction was cooled to room temperature. The crude product was passed through a short $SiO_2$ plug using hexanes as eluent, and the product was recrystallized from hexanes yielding 4,8-didodecylbenzo[1,2-b:4,5-b']dithiophene as a white solid (1.6 grams, 27% yield). The structure was confirmed by $^1H$ and $^{13}C$ NMR spectroscopy.

Example 4

In a 500 mL 3-necked round-bottomed flask anhydrous THF (300 ml) treated with a 1M solution of dodecylmagnesium bromide (68.1 ml, 68.1 mmol) under an argon atmosphere. The reaction was treated with solid 4,8-dehydrobenzo[1,2-b:4,5-b']dithiophene-4,8-dione (5.00 grams, 22.7 mmol) and stirred at room temperature. After 1 hour, the reaction was heated to 65° C. After 1 hour, the heating bath was removed and the reaction was cooled to room temperature and carefully quenched with water (20 mL). The reaction was treated with a solution of tin(II) chloride (21.52 grams, 113 mmol) in 10 vol % HCl (50 ml) in one portion and the reaction was heated to 65° C. After 3 hours, the heating bath was removed and the reaction was cooled to room temperature. The layers were separated and the organic layer was dried (using $MgSO_4$), filtered and concentrated using a rotary evaporator. The crude product was passed through a short $SiO_2$ plug using hexanes as eluent, and the product was recrystallized from hexanes yielding 4,8-didodecylbenzo[1,2-b:4,5-b']dithiophene as a white solid (3.2 grams, 27% yield). The structure was confirmed by $^1H$ and $^{13}C$ NMR spectroscopy.

Example 5

In a 250 mL 3 necked round-bottomed flask a mixture of toluene (80 ml) and 2M $Na_2CO_3$ (40.0 ml) was deoxygenated by bubbling argon through the solution. After 1 hour, the reaction was treated with 2,6-dibromo-4,8-didodecylbenzo[1,2-b:4,5-b']dithiophene (3.00 grams, 4.38 mmol), 3-dodecylthiophene-2-boronic acid pinacol ester (4.15 grams, 10.95 mmol), $Pd(PPh_3)_4$ (0.253 grams, 0.22 mmol) and heated at 100° C. under an argon atmosphere. After 48 hours, the heating bath was removed and the reaction was cooled to room temperature. The layers were separated and the aqueous phase was extracted with ethyl acetate (75 mL). The combined organic layers were dried (using $MgSO_4$), filtered and concentrated using a rotary evaporator. The crude product was purified by column chromatography through $SiO_2$ using hexanes as eluent, and recrystallized from hexanes yielding 4,8-didodecyl-2,6-bis(3-dodecylthien-2-yl)benzo[1,2-b:4,5-b']dithiophene as a yellow solid (3.5 g, 78%). The structure was confirmed by $^1H$ and $^{13}C$ NMR spectroscopy. The purity of the monomer was 94% as determined by HPLC.

Example 6

To form a polymer of Formula (II), 4,8-didodecyl-2,6-bis(3-dodecylthien-2-yl)benzo[1,2-b:4,5-b']dithiophene was polymerized using $FeCl_3$. After purification, the polymer was used as a p-type semiconductor layer in top contact OTFT devices. The mobility range of the material was measured to be 0.239-0.285 $cm^2/V\cdot sec$, which was consistent with a control sample. This example showed that BDT building blocks prepared using this new process can be incorporated into electronic grade materials without compromising performance.

The devices, polymers, and processes of the present disclosure have been described with reference to exemplary embodiments. Obviously, modifications and alterations will occur to others upon reading and understanding the preceding detailed description. It is intended that the exemplary embodiments be construed as including all such modifications and alterations insofar as they come within the scope of the appended claims or the equivalents thereof.

The invention claimed is:

1. A method of producing a semiconductor polymer of Formula (II):

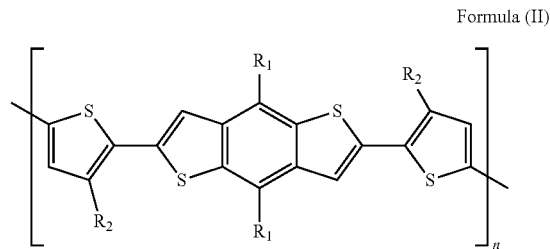

Formula (II)

wherein $R_1$ and $R_2$ are independently selected from alkyl, aryl, and heteroaryl; and n is from 2 to about 5,000; the method comprising:
reacting a benzoquinone-dithiophene with a reagent of the formula M-$R_1$, wherein M is MgX or Li, X is a halogen, and $R_1$ is alkyl, aryl, or heteroaryl;
reducing the resulting intermediate to form the 4,8-disubstituted benzodithiophene of Formula (I):

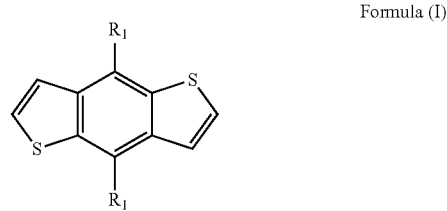

Formula (I)

coupling a 3-$R_2$-thiophene to the 2 and 6 positions of the benzodithiophene, wherein $R_2$ is alkyl, aryl, or heteroaryl, to obtain a repeating unit; and
polymerizing the repeating unit to obtain the polymer of Formula (II).

2. The method of claim 1, wherein $R_1$ and $R_2$ independently have from 1 to about 24 carbon atoms.

3. The method of claim 1, wherein the 4,8-disubstituted benzodithiophene of Formula (I) is coupled to 3-$R_2$-thiophene at the 2 and 6 positions using a palladium, nickel, or iron catalyzed cross-coupling reaction.

4. The method of claim 1, further comprising purifying the repeating unit of Formula (II) (n=1) to a minimum HPLC purity of 94% using column chromatography through silica gel, alumina, or combinations thereof; recrystallization; and combinations thereof.

5. The method of claim 1, wherein $R_1$ and $R_2$ are each alkyl having from 1 to about 24 carbon atoms.

6. The method of claim 5, wherein $R_1$ and $R_2$ are identical.

7. The method of claim 1, wherein $R_1$ is linear alkyl or branched alkyl.

8. The method of claim 1, wherein the reduction of the intermediate is performed using a metal chloride in an acidic solution, the metal chloride being selected from the group consisting of tin chloride, zinc chloride, or iron chloride.

9. The method of claim 1, wherein the reagent is dissolved in a solvent selected from hydrocarbon solvents, aromatic solvents, diethyl ether, tert-butylmethyl ether, tetrahydrofuran, 1,4-dioxane, and mixtures thereof to form a reagent solution.

10. The method of claim 1, further comprising adding a salt or organic additive to the reagent solution to modify the reactivity of the reagent.

11. The method of claim 10, wherein the salt is LiCl or LiBr.

12. The method of claim 1, wherein the reacting is performed by adding the benzoquinone-dithiophene to the reagent solution.

13. The method of claim 1, wherein the reacting comprises combining the benzoquinone-dithiophene with the reagent and heating to a temperature of from about 20° C. to about 140° C.

14. The method of claim 13, wherein the heating occurs for a period of at least 30 minutes.

15. The method of claim 1, wherein the molar ratio of the reagent to the benzoquinone-dithiophene is from about 2:1 to about 4:1.

16. The method of claim 1, wherein the reducing comprises heating to a temperature of from about 20° C. to about 140° C.

17. The method of claim 16, wherein the heating occurs for a period of at least 30 minutes.

18. The method of claim 1, further comprising purifying the 4,8-disubstituted benzodithiophene using column chromatography through silica gel, alumina, or combinations thereof; recrystallization; and combinations thereof.

* * * * *